(12) United States Patent
Melzer et al.

(10) Patent No.: US 8,569,320 B2
(45) Date of Patent: Oct. 29, 2013

(54) TOPICAL COMPOSITION FOR THE TREATMENT OF ACTINIC KERATOSIS

(75) Inventors: Manfred Melzer, Reinbek (DE); Carmen Matthies, Woltersdorf (DE); Klaus Treudler, Seevetal (DE); Christoph Willers, Hamburg (DE); Henning Mallwitz, Buchholz/N. (DE)

(73) Assignee: Almirall Hermal GmbH, Reinbek (DE)

( * ) Notice: Subject to any disclaimer, the term of this patent is extended or adjusted under 35 U.S.C. 154(b) by 125 days.

(21) Appl. No.: 13/002,971

(22) PCT Filed: Jun. 29, 2009

(86) PCT No.: PCT/EP2009/004682
§ 371 (c)(1), (2), (4) Date: Mar. 21, 2011

(87) PCT Pub. No.: WO2010/003568
PCT Pub. Date: Jan. 14, 2010

(65) Prior Publication Data
US 2011/0301130 A1   Dec. 8, 2011

(30) Foreign Application Priority Data

Jul. 7, 2008 (EP) ..................... 08012237

(51) Int. Cl.
*A61K 31/505* (2006.01)
(52) U.S. Cl.
USPC ................ 514/274; 514/163; 514/161
(58) Field of Classification Search
USPC ......................... 514/161, 163, 274
See application file for complete search history.

(56) References Cited

U.S. PATENT DOCUMENTS

| | | | |
|---|---|---|---|
| 2,802,005 A | 8/1957 | Heidelberger et al. | |
| 4,234,599 A | 11/1980 | Van Scott et al. | |
| 5,091,171 A | 2/1992 | Yu et al. | |
| 5,167,649 A | 12/1992 | Zook | |
| 5,627,187 A * | 5/1997 | Katz | 514/274 |
| 6,462,071 B1 * | 10/2002 | Castillejos | 514/413 |
| 2005/0137164 A1 | 6/2005 | Arkin et al. | |
| 2007/0027194 A1 | 2/2007 | Easterling et al. | |
| 2007/0053984 A1 | 3/2007 | Spann-Wade et al. | |
| 2007/0264317 A1 | 11/2007 | Yosha et al. | |

FOREIGN PATENT DOCUMENTS

| | | |
|---|---|---|
| EP | 0391033 A2 | 10/1990 |
| WO | 9632112 A1 | 10/1996 |
| WO | 2006134406 A1 | 12/2006 |

OTHER PUBLICATIONS

The Skin Cancer Foundation Article entitled "Lo Que Usted Debe Conocer Acerca De Este Precancer Comun de la piel" (2002).
Merck Manual Professional Article entitled "Chronic Effects of Sunlight", Section: Dermatologic Disorders, Chapter Reactions to Sunlight (Published Aug. 2007) (2 pages).

* cited by examiner

*Primary Examiner* — Rei-tsang Shiao
(74) *Attorney, Agent, or Firm* — Hovey Williams LLP

(57) ABSTRACT

The invention relates to a topical gel composition for use in the treatment of actinic keratosis comprising (a) an active agent for treatment of actinic keratosis, (b) a keratolytically active agent, (c) a gel former, and (d) an organic solvent.

29 Claims, No Drawings

TOPICAL COMPOSITION FOR THE TREATMENT OF ACTINIC KERATOSIS

CROSS-REFERENCE TO RELATED APPLICATION(S)

This is a National Phase Application pursuant to 37 C.F.R. §371 of International Application No. PCT/EP2009/004682, filed Jun. 29, 2009, claiming priority from European Application No. EP 08012237.7, filed Jul. 7, 2008, the entire disclosures of both of which are hereby incorporated by reference herein.

BACKGROUND OF THE INVENTION

1. Field of the Invention

The invention relates to a topical composition for use as a medicament for the treatment of actinic keratosis.

2. Discussion of the Prior Art

Actinic keratosis is a carcinoma in situ of the epidermis. It concerns a proliferation of transformed keratinocytes restricted to the epidermis, which is characterized by a high rate of mutation of inter alia the tumor suppresser gene p53 and the telomerase gene. It is further associated with characteristic chromosomal aberrations which are typically also found in invasive squamous cell carcinomas of the skin. In about 10% of all patients suffering from actinic keratosis, and particularly in about 30% of the patients with additional immune suppression, a squamous cell carcinoma of the skin develops during the further development of the condition. Thus, a diagnosis of actinic keratosis generally constitutes an indication for treatment.

In the therapy of actinic keratosis, different surgical and physical methods such as cryosurgery, curettage, excision therapy, laser therapy and soft X-ray therapy have been described. Moreover, different forms of pharmacotherapy for the treatment of actinic keratosis are known. For instance, cyclooxygenase inhibitors such as diclofenac, anti-metabolites such as 5'-fluorouracil and immune modulators such as imiquimod have been used for the treatment of actinic keratoses.

Pharmacotherapy of actinic keratosis is often effected by topical application of the corresponding drugs, particularly in the form of water based creams and gels or in the form of alcoholic solutions.

Regarding water based cream and gel formulations known in the state of the art, it has been found to be disadvantageous that these formulations have to be rubbed into the skin. In the process of rubbing in a cream or gel formulation, an active agent comprised therein is typically distributed over a large area of skin. Therefore, it is hardly possible to apply water based cream or gel formulations specifically to the skin areas actually in need of treatment. With respect to alcoholic solutions, it has been found that these formulations tend to run, particularly in the application to head and face areas where actinic keratosis occur particularly often. Thus, alcoholic solutions are not amenable to accurate dosing of active agents either. Because of their inadequate suitability for specific dosing, formulations according to the state of the art are contacted with unnecessarily large areas of skin which increases the degree and risk of side effects. Furthermore, it has been found that drugs such as 5'-fluorouracil tend to crystallize out from aqueous or alcoholic formulation when stored in that form for a period of time corresponding to the typical shelf life of such formulations. WO-A-96/32112 discloses compositions for treating actinic damage to the skin comprising 5'-fluorouracil, a superficial skin peeling agent and a pharmaceutically acceptable carrier, in particular in the form of an alcoholic solution. For the treatment of acute actinic keratoses, 5'-fluorouracil contents of 5 to 10% are suggested. It has been found that topical application of compositions comprising 5'-fluorouracil in these amounts induces substantial side effects. Furthermore, the described alcoholic solution tends to run when topically applied to the surface of the skin.

There is a need for topical compositions suitable for use as a medicament for the treatment of actinic keratosis having high efficiency in the treatment with minimal side effects and allowing for exact dosing.

DETAILED DESCRIPTION OF THE PREFERRED EMBODIMENTS

The present invention therefore provides a topical gel composition comprising
(a) an active agent for the treatment of actinic keratosis,
(b) a keratolytically active agent,
(c) a gel former, and
(d) an organic solvent
for use in the treatment of actinic keratosis.

The composition is typically in a form for direct application to the skin. Thus, the composition is preferably not encapsulated such as by a patch or plaster.

It is preferred that the composition comprises less than 5 wt.-%, particularly less than 1 wt.-%, more preferably less than 0.5 wt.-% water. It is particularly preferred that the composition is substantially free of water.

The specific combination of components in the composition according to the invention has a number of advantages. Particularly, this combination results in a high pharmacological availability of the active agent allowing for compositions which, despite a relatively low drug content, have a high efficiency in the treatment of actinic keratosis. Moreover, the compositions can be accurately dosed both with respect to the amount applied as well as the skin area targeted. The compositions are further advantageous in that they are absorbed or dried quickly, that they do not require rubbing into the skin, and that they do not run even when applied, for instance, in vertical head and/or face areas. Particularly, it has been found that only minimal side effects are observed in the use of the composition according to the invention. Moreover, the compositions according to the invention are stable over typical periods of storage, such as for 3 years, even when active agents such as 5'-fluorouracil are used.

The composition according to the invention is present in the form of a gel. The gel generally has any viscosity suitable for the product to be applied, for instance with a brush, onto a skin area affected by actinic keratosis without running of the composition. A composition having a viscosity in the range of 300 to 1500 mPas at 20° C., particularly 500 to 1200 mPas at 20° C., most preferably 600 to 900 mPas at 20° C. is particularly preferred. Viscosity is measured preferably with a DIN measuring system Z3 at conditions of $D=57.2 \text{ sec}^{-1}$ and $T=20°$ C. Such a gel can be dosed particularly accurately without running when topically applied.

According to the invention, a composition is preferred wherein the active agent for treatment of actinic keratosis is selected from the group consisting of cyclooxygenase inhibitors, topical immune modulators, antimetabolites, and mixtures thereof. Examples of suitable cyclooxygenase inhibitors are ibuprofen, diclofenac, etodolac, celecoxib and piroxicam. Examples of topical immune modulators include imiquimod, resimiquimod and sotirimod. Preferred antimetabolites are antimetabolites having a pyrimidine structure, particularly 5'-fluorouracil.

It is particularly preferred that the active agent for treatment of actinic keratosis is selected from the group consisting of antimetabolites having a pyrimidine structure, wherein 5'-fluorouracil is particularly preferred. Moreover, it is preferred that the composition comprises 0.1 to 10 wt.-%, particularly 0.25 to 4.5 wt.-%, of the active agent for treatment of actinic keratosis. In a preferred embodiment of the invention, the composition comprises less than 2 wt.-% of the active agent for treatment of actinic keratosis. Most preferably, the composition comprises 0.4 to 1 wt.-% of an active agent for treatment of actinic keratosis. Surprisingly, the compositions according to the invention are highly efficient in the treatment of actinic keratosis even with relatively low drug contents.

The composition comprises at least one keratolytically active agent. The term "keratolytically active agent" as used herein refers to an agent which is suitable to effect the dissolution and detachment of korneocytes from the stratum corneum.

Preferably, the keratolytically active agent is selected from the group consisting of retinoid receptor agonists, urea, organic acids, particularly hydroxy carboxylic acids, and mixtures thereof. Examples of suitable retinoid receptor agonists include adapalene and retinoids, particularly tretinoin, isotretinoin, motretinide, tazarotene and/or retinol. Particularly preferred organic acids are glycolic acid, acetic acid, lactic acid and/or salicylic acid. Salicylic acid is especially preferred. Moreover, it is preferred that the composition comprises 0.025 to 30 wt.-%, particularly 0.1 to 20 wt.-%, more preferably 2 to 20 wt.-%, most preferably 5 to 15 wt.-% of a keratolytically active agent.

The composition further comprises at least one gel former. The term "gel former" as used herein refers to a component of the composition which together with the organic solvent will form a viscoelastic mass consisting of colloidal suspensions. Different gel formers are suitable for use in the composition according to the invention. A composition is particularly preferred wherein the gel former is selected from the group consisting of vinyl homopolymers and copolymers, cellulose derivatives, and mixtures thereof.

It is particularly preferred that the vinyl homopolymers and copolymers are copolymers based on acrylic acid or methacrylic acid or esters thereof and methyl methacrylate. Examples of suitable copolymers based on acrylic acid or methacrylic acid or esters thereof and methyl methacrylate are ethyl acrylate-methyl methacrylate copolymer (Eudragit NE), methacrylic acid-methylmethacrylate copolymer (Eudragit L, Eudragit S or Rohagit S), and butyl methacrylate-methyl methacrylate copolymer (Plastoid B), preferably Plastoid B.

Preferred cellulose derivatives are cellulose esters, such as cellulose nitrate. According to a preferred embodiment, the composition according to the invention comprises at least one gel former selected from the group consisting copolymers based on acrylic acid or methacrylic acid or esters thereof and methyl methacrylate, and at least one gel former selected from the group consisting of cellulose derivatives. It has been found that such combination of gel formers is particularly able to form, together with the organic solvent, a gel which can be accurately dosed, does not require rubbing into the skin and does not run when topically applied.

It is particularly preferred that the composition according to the invention comprises 1 to 30 wt.-%, particularly 2 to 20 wt.-%, most preferably 5 to 15 wt.-% of a gel former.

The composition according to the invention comprises at least one organic solvent. It is preferred that the organic solvent is selected from the group consisting of $C_1$-$C_{10}$ alcohols, esters of $C_1$-$C_{10}$ alcohols with $C_1$-$C_{10}$ carboxylic acids, $C_3$-$C_8$ alkyl ketones, and mixtures thereof. Examples of suitable solvents include ethanol, isopropanol, butanol, ethyl acetate, butyl acetate and acetone. Preferably, the organic solvent comprises a $C_1$-$C_6$ alcohol and an ester of $C_1$-$C_6$ alcohol with a $C_2$-$C_6$ carboxylic acid. It is particularly preferred that the organic solvent has a boiling point of below 100° C., particularly below 90° C., most preferably below 80° C.

It is further preferred that the composition comprises 1 to 90 wt.-%, particularly 50 to 80 wt.-%, most preferably 60 to 75 wt.-% of an organic solvent. It has surprisingly been found that the solvent used according to the invention in combination with the gel former provides a high availability of the active agent and further provides a composition which can be accurately dosed, does not require rubbing into the skin and does not run when topically applied.

According to a preferred embodiment, the composition according to the invention further comprises a skin penetration enhancer. It is preferred that the skin penetration enhancer is selected from the group consisting of polyvalent aliphatic $C_2$-$C_{10}$ alcohols, polyalkylene glycols with $C_2$-$C_4$ alkylene groups, non-alkoxylated ethers of polyvalent aliphatic $C_2$-$C_{10}$ alcohols and polyalkylene glycols with $C_2$-$C_4$ alkylene groups, azones, terpenes, terpenoids, pyrrolidones, sulfoxides, and mixtures thereof. It has been found that the presence of a skin penetration enhancer in the composition according to the invention further improves availability of the active agent and allows for a reduction of the amount of active agent while maintaining the pharmacological effect.

It is particularly preferred that the skin penetration enhancer comprises a sulfoxide, particularly dimethyl sulfoxide. Examples of further skin penetration enhancers are polyvalent alcohols, particularly $C_2$-$C_8$ glycols, such as propylene glycol or butylene glycol, and glycerol. It is further preferred that the composition comprises 1 to 50 wt.-%, particularly 3 to 15 wt.-%, most preferably 5 to 10 wt.-% of a skin penetration enhancer.

According to a particularly preferred embodiment, the composition comprises
  (a) 0.25 to 4.5 wt.-%, particularly 0.4 to 1 wt.-%, of the active agent for treatment of actinic keratosis, preferably 5'-fluorouracil,
  (b) 2 to 20 wt.-%, particularly 5 to 15 wt.-%, of the keratolytically active agent, preferably salicylic acid,
  (c) 2 to 20 wt.-%, particularly 5 to 15 wt.-%, of the gel former, preferably a combination of a (meth)acrylate homopolymer or copolymer and a cellulose derivative,
  (d) 40 to 70 wt.-%, particularly 50 to 60 wt.-%, of an ester of a $C_1$-$C_4$ alcohol with a $C_2$-$C_4$ carboxylic acid,
  (e) 5 to 30 wt.-%, particularly 10 to 20 wt.-%, of a $C_1$-$C_4$ alcohol, and
  (f) 3 to 15 wt.-%, particularly 5 to 10 wt.-%, of the skin penetration enhancer, preferably dimethyl sulfoxide.

The composition may moreover comprise further customary pharmaceutically acceptable components. However, oil components such as mineral oil are generally less desirable in the composition because they may cause an undesirable skin feeling and may be comedogenic. Therefore, it is generally preferred that the composition comprises less than 5 wt.-%, particularly less than 1 wt.-%, more preferably less than 0.1 wt.-% of an oil component. It is particularly preferred that the composition is substantially free of oil.

The invention also relates to a method of treating actinic keratosis in a patient, which method comprises applying to the affected area of skin a topical gel composition according to the invention.

The invention also relates to the use of the composition of the present invention in the manufacture of a medicament for the treatment of actinic keratosis.

The invention is further described in more detail with reference to the following examples, which do not limit the scope of the invention in any way:

Example 1

A product was prepared having the following composition (wt.-%):

| | |
|---|---|
| 5'-Fluorouracil | 0.50 |
| Salicylic acid | 10.00 |
| Poly(butyl methacrylate, methyl methacrylate) | 4.00 |
| Cellulose nitrate | 5.00 |
| Dimethyl sulfoxide | 8.00 |
| Ethylacetate | 56.50 |
| Ethanol | 16.00 |

Example 2

A product was prepared having the following composition (wt.-%):

| | |
|---|---|
| 5'-Fluorouracil | 0.50 |
| Salicylic acid | 10.00 |
| Poly(butyl methacrylate, methyl methacrylate) | 5.00 |
| Cellulose nitrate | 4.00 |
| Dimethyl sulfoxide | 10.00 |
| Ethylacetate | 54.50 |
| Ethanol | 16.00 |

Example 3

A product was prepared having the following composition (wt.-%):

| | |
|---|---|
| 5'-Fluorouracil | 0.50 |
| Salicylic acid | 10.00 |
| Poly(butyl methacrylate, methyl methacrylate) | 5.00 |
| Cellulose nitrate | 4.00 |
| Dimethyl sulfoxide | 8.00 |
| Ethylacetate | 56.50 |
| Ethanol | 16.00 |

Example 4

A product was prepared having the following composition (wt.-%):

| | |
|---|---|
| 5'-Fluorouracil | 0.50 |
| Lactic acid | 10.00 |
| Poly(butyl methacrylate, methyl methacrylate) | 5.00 |
| Cellulose nitrate | 4.00 |
| Dimethyl sulfoxide | 8.00 |
| Ethylacetate | 56.50 |
| Ethanol | 16.00 |

Example 5

A product was prepared having the following composition (wt.-%):

| | |
|---|---|
| 5'-Fluorouracil | 0.50 |
| Lactic acid | 5.00 |
| Salicylic acid | 5.00 |
| Poly(butyl methacrylate, methyl methacrylate) | 5.00 |
| Cellulose nitrate | 4.00 |
| Dimethyl sulfoxide | 8.00 |
| Ethylacetate | 56.50 |
| Ethanol | 16.00 |

Example 6

A product was prepared having the following composition (wt.-%):

| | |
|---|---|
| Ibuprofen | 0.50 |
| Salicylic acid | 10.00 |
| Poly(butyl methacrylate, methyl methacrylate) | 5.00 |
| Cellulose nitrate | 4.00 |
| Dimethyl sulfoxide | 8.00 |
| Ethylacetate | 56.50 |
| Ethanol | 16.00 |

Example 7

A product was prepared having the following composition (wt.-%):

| | |
|---|---|
| 5'-Fluorouracil | 0.50 |
| Salicylic acid | 10.00 |
| Poly(butyl methacrylate, methyl methacrylate) | 4.00 |
| Cellulose nitrate | 5.00 |
| Dimethyl sulfoxide | 10.00 |
| Ethylacetate | 56.50 |
| Ethanol | 14.00 |

The products obtained were in the form of a gel having a viscosity of about 770 mPas at 20° C. The products could be accurately applied onto actinic keratosis with a fine brush. Due to evaporation of solvents, the gel quickly formed a film on the skin without running.

The invention claimed is:

1. A method of treating actinic keratosis in a patient, said method comprising the step of:
   applying a topical gel composition to the affected area of skin, wherein the topical gel composition comprises:
   (a) 0.25 to 4.5 wt.-% of an active agent for treatment of actinic keratosis selected from the group consisting of cyclooxygenase inhibitors, topical immune modulators, antimetabolites, and mixtures thereof,
   (b) a keratolytically active agent selected from the group consisting of retinoid receptor agonists, urea, organic acids, and mixtures thereof, (c) a gel former, wherein the viscosity of the gel is in the range of 300 to 1500 m Pas at 20° C., and (d) an organic solvent, wherein said topical gel composition comprises less than 5 wt.-% water.

2. The method according to claim 1, wherein the active agent for treatment of actinic keratosis is selected from the group consisting of ibuprofen, diclofenac, etodolac, celecoxib, piroxicam, imiquimod, resimiquimod, sotirimod, and 5'-fluorouracil.

3. The method according to claim 1, wherein the keratolytically active agent is selected from the group consisting of adapalene, tretinoin, isotretinoin, motretinide, tazarotene, retinol, urea, glycolic acid, acetic acid, lactic acid, salicylic acid, and mixtures thereof.

4. The method according to claim 1, wherein the composition comprises less than 1 wt.-% water.

5. The method according to claim 4, wherein the composition is substantially free of water.

6. The method according to claim 1, wherein the viscosity of the gel is in the range of 300 to 1500 mPas at 20° C.

7. The method according to claim 6, wherein the viscosity of the gel is in the range of 600 to 900 mPas at 20° C.

8. The method according to claim 1, wherein the active agent for treatment of actinic keratosis is 5'-fluorouracil.

9. The method according to claim 1, wherein the composition comprises 0.4 to 1 wt.-% of the active agent for treatment of actinic keratosis.

10. The method according to claim 1, wherein the keratolytically active agent is selected from the group consisting of glycolic acid, acetic acid, lactic acid, salicylic acid, and mixtures thereof.

11. The method according to claim 1, wherein the keratolytically active agent is salicylic acid.

12. The method according to claim 1, wherein the composition comprises 0.025 to 30 wt.-% of the keratolytically active agent.

13. The method according to claim 12, wherein the composition comprises 5 to 15 wt.-% of the keratolytically active agent.

14. The method according to claim 1, wherein the gel former is selected from the group consisting of vinyl homopolymers and copolymers, cellulose derivatives, and mixtures thereof.

15. The method according to claim 1, wherein the composition comprises 1 to 30 wt.-% of the gel former.

16. The method according to claim 15, wherein the composition comprises 5 to 15 wt.-% of the gel former.

17. The method according to claim 1, wherein the organic solvent is selected from the group consisting of $C_1$-$C_{10}$ alcohols, esters of $C_1$-$C_{10}$ alcohols with $C_1$-$C_{10}$ carboxylic acids, and mixtures thereof.

18. The method according to claim 17, wherein the organic solvent comprises a $C_1$-$C_6$ alcohol and an ester of $C_1$-$C_6$ alcohol with a $C_2$-$C_6$ carboxylic acid.

19. The method according to claim 1, wherein the boiling point of the organic solvent is below 100° C.

20. The method according to claim 19, wherein the boiling point of the organic solvent is below 80° C.

21. The method according to claim 1, wherein the composition comprises 1 to 90 wt.-% of the organic solvent.

22. The method according to claim 21, wherein the composition comprises 60 to 75 wt.-% of the organic solvent.

23. The method according to claim 1, said composition further comprising a skin penetration enhancer.

24. The method according to claim 23, wherein the skin penetration enhancer is selected from the group consisting of polyvalent aliphatic $C_2$-$C_{10}$ alcohols, polyalkylene glycols having $C_2$-$C_4$ alkylene groups, nonalkoxylated ethers of polyvalent aliphatic $C_2$-$C_{10}$ alcohols and polyalkylene glycols having $C_2$-$C_4$ alkylene groups, azones, terpenes, terpenoides, pyrrolidones, sulfoxides, and mixtures thereof.

25. The method according to claim 24, wherein the skin penetration enhancer is dimethyl sulfoxide.

26. The method according to claim 23, wherein the composition comprises 1 to 50 wt.-% of the skin penetration enhancer.

27. The method according to claim 26, wherein the composition comprises 5 to 10 wt.-% of the skin penetration enhancer.

28. The method according to claim 1, wherein the composition comprises:

0.25 to 4.5 wt.-% of the active agent for treatment of actinic keratosis, 2 to 20 wt.-% of the keratolytically active agent, 2 to 20 wt.-% of the gel former, 40 to 70 wt.-% of an ester of a $C_1$-$C_4$ alcohol with a $C_2$-$C_4$ carboxylic acid, 5 to 30 wt.-% of a $C_1$-$C_4$ alcohol, and 3 to 15 wt.-% of the skin penetration enhancer.

29. The method according to claim 8, wherein the composition comprises:

0.25 to 4.5 wt.-% of 5'-fluorouracil, 2 to 20 wt.-% of salicylic acid, 2 to 20 wt.-% of gel former comprising a combination of a (meth)acrylate homopolymer or copolymer and a cellulose derivative, 40 to 70 wt.-% of an ester of a $C_1$-$C_4$ alcohol with a $C_2$-$C_4$ carboxylic acid, 5 to 30 wt.-% of a $C_1$-$C_4$ alcohol, and 3 to 15 wt.-% of dimethylsulfoxide.

* * * * *